US010193209B2

(12) United States Patent
Blair

(10) Patent No.: US 10,193,209 B2
(45) Date of Patent: Jan. 29, 2019

(54) MAT BASED ANTENNA AND HEATER SYSTEM, FOR USE DURING MEDICAL PROCEDURES

(71) Applicant: Covidien LP, Mansfield, MA (US)

(72) Inventor: William A. Blair, San Diego, CA (US)

(73) Assignee: Covidien LP, Mansfield, MA (US)

( * ) Notice: Subject to any disclaimer, the term of this patent is extended or adjusted under 35 U.S.C. 154(b) by 461 days.

(21) Appl. No.: 15/062,671

(22) Filed: Mar. 7, 2016

(65) Prior Publication Data

US 2016/0294040 A1    Oct. 6, 2016

Related U.S. Application Data

(60) Provisional application No. 62/143,726, filed on Apr. 6, 2015.

(51) Int. Cl.
*H01Q 1/22* (2006.01)
*H01Q 7/00* (2006.01)
(Continued)

(52) U.S. Cl.
CPC ............... *H01Q 1/22* (2013.01); *A61B 90/98* (2016.02); *A61F 7/007* (2013.01); *A61F 7/08* (2013.01);
(Continued)

(58) Field of Classification Search
CPC .. H01Q 3/26; H01Q 7/00; H01Q 9/27; H01Q 21/061
See application file for complete search history.

(56) References Cited

U.S. PATENT DOCUMENTS

| 3,717,876 A | 2/1973 | Volkers et al. |
| 3,783,282 A | 1/1974 | Hoppenstein |

(Continued)

FOREIGN PATENT DOCUMENTS

| AU | 716011 B2 | 2/2000 |
| CN | 2865741 Y | 2/2007 |

(Continued)

OTHER PUBLICATIONS

Black, "Method and Apparatus to Account for Transponder Tagged Objects During Clinical Procedures, Employing a Trocar," U.S. Appl. No. 62/360,869, filed Jul. 11, 2016, 99 pages.

(Continued)

*Primary Examiner* — Hoang Nguyen

(57) ABSTRACT

A mat based antenna and heater system allows medical personnel to ascertain the presence or absence of objects (e.g., medical implements, sponges) tagged with transponders during medical procedures (e.g., surgery, labor and delivery), and may allow reading of information from the transponders, writing information to the transponders and/or controlling or commanding the transponders. In use, the mat based antenna and heater system may be positioned beneath a patient, such as during surgery or child birth. A controller is coupled to the antennas to transmit signals (e.g. interrogation signals) to the transponders and to receive signals (e.g., response signals) from the transponders. The controller also operates one or more heaters or heating elements to selectively provide warmth to a patient. One or more sensors can detect temperatures at one or more locations, and the controller can use temperature readings in as feedback in controlling the heaters or heating elements.

26 Claims, 5 Drawing Sheets

(51) Int. Cl.
*H04B 5/00* (2006.01)
*A61F 7/00* (2006.01)
*A61F 7/08* (2006.01)
*A61B 90/98* (2016.01)

(52) U.S. Cl.
CPC ............. *H01Q 1/2216* (2013.01); *H01Q 7/00* (2013.01); *H04B 5/0062* (2013.01); *A61F 2007/0071* (2013.01)

(56) References Cited

U.S. PATENT DOCUMENTS

| | | | |
|---|---|---|---|
| 3,984,695 A | 10/1976 | Collica et al. |
| 4,034,297 A | 7/1977 | Giorgi et al. |
| 4,355,317 A | 10/1982 | Muzio |
| 4,603,074 A | 7/1986 | Pate et al. |
| 4,681,111 A | 7/1987 | Silvian |
| 4,788,730 A | 12/1988 | Bexton |
| 4,992,675 A | 2/1991 | Conner, Jr. et al. |
| 5,057,095 A | 10/1991 | Fabian |
| 5,353,011 A | 10/1994 | Wheeler et al. |
| 5,664,582 A | 9/1997 | Szymaitis |
| 6,073,284 A | 6/2000 | Borders |
| 6,172,608 B1 | 1/2001 | Cole |
| 6,201,469 B1 | 3/2001 | Balch et al. |
| 6,232,878 B1 | 5/2001 | Rubin |
| 6,349,234 B2 | 2/2002 | Pauly et al. |
| 6,359,562 B2 | 3/2002 | Rubin |
| 6,401,283 B2 | 6/2002 | Thomas et al. |
| 6,578,219 B1 | 6/2003 | Gabel et al. |
| 6,588,661 B2 | 7/2003 | Degrauwe et al. |
| 6,599,448 B1 | 7/2003 | Ehrhard, Jr. et al. |
| 6,620,187 B2 | 9/2003 | Carson et al. |
| 6,632,216 B2 | 10/2003 | Houzego et al. |
| 6,633,226 B1 | 10/2003 | Nysen |
| 6,645,232 B2 | 11/2003 | Carson |
| 6,648,905 B2 | 11/2003 | Hoglund et al. |
| 6,653,607 B2 | 11/2003 | Ellis et al. |
| 6,660,027 B2 | 12/2003 | Gruszecki et al. |
| 6,669,715 B2 | 12/2003 | Hoglund et al. |
| 6,692,518 B2 | 2/2004 | Carson |
| 6,696,954 B2 | 2/2004 | Chung |
| 6,699,267 B2 | 3/2004 | Voorhees et al. |
| 6,722,783 B2 | 4/2004 | Jackson, Sr. |
| 6,744,378 B1 | 6/2004 | Tyburski |
| 6,753,783 B2 | 6/2004 | Friedman et al. |
| 6,774,800 B2 | 8/2004 | Friedman et al. |
| 6,799,063 B2 | 9/2004 | Carson |
| 6,812,824 B1 | 11/2004 | Goldinger et al. |
| 6,812,842 B2 | 11/2004 | Dimmer |
| 6,814,889 B1 | 11/2004 | O'Grady et al. |
| 6,822,570 B2 | 11/2004 | Dimmer et al. |
| 6,832,398 B2 | 12/2004 | Borders et al. |
| 6,838,990 B2 | 1/2005 | Dimmer |
| 6,861,954 B2 | 3/2005 | Levin |
| 6,879,300 B2 | 4/2005 | Rochelle et al. |
| 6,903,656 B1 | 6/2005 | Lee |
| 6,909,366 B1 | 6/2005 | Marsh et al. |
| 6,912,749 B2 | 7/2005 | Thomas et al. |
| 6,918,144 B2 | 7/2005 | Friedman |
| 6,924,467 B2 | 8/2005 | Ellis et al. |
| 6,933,469 B2 | 8/2005 | Ellis et al. |
| 6,951,305 B2 | 10/2005 | Overhultz et al. |
| 6,967,309 B2 | 11/2005 | Wyatt et al. |
| 6,974,935 B2 | 12/2005 | O'Grady |
| 6,977,504 B2 | 12/2005 | Wright et al. |
| 6,988,284 B2 | 1/2006 | Bannister |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,071,791 B1 | 7/2006 | Wilson, III |
| 7,098,793 B2 | 8/2006 | Chung |
| 7,098,866 B2 | 8/2006 | Desjeux et al. |
| 7,142,815 B2 | 11/2006 | Desjeux et al. |
| 7,158,030 B2 | 1/2007 | Chung |
| 7,158,754 B2 | 1/2007 | Anderson |
| 7,159,832 B2 | 1/2007 | Easterling |
| 7,160,258 B2 | 1/2007 | Imran et al. |
| 7,176,419 B2 | 2/2007 | Ellis et al. |
| 7,176,798 B2 | 2/2007 | Dimmer et al. |
| 7,196,289 B2 | 3/2007 | Ellis et al. |
| 7,227,469 B2 | 6/2007 | Varner et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,299,981 B2 | 11/2007 | Hickle et al. |
| 7,319,396 B2 | 1/2008 | Homanfar et al. |
| 7,319,397 B2 | 1/2008 | Chung et al. |
| 7,319,398 B2 | 1/2008 | Marino |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| 7,382,255 B2 | 6/2008 | Chung |
| 7,397,364 B2 | 7/2008 | Govari |
| 7,420,468 B2 | 9/2008 | Fabian et al. |
| 7,423,535 B2 | 9/2008 | Chung et al. |
| 7,446,646 B2 | 11/2008 | Huomo |
| 7,464,713 B2 | 12/2008 | Fabian et al. |
| 7,480,950 B2 | 1/2009 | Feher |
| 7,492,257 B2 | 2/2009 | Tethrake et al. |
| 7,492,261 B2 | 2/2009 | Cambre et al. |
| 7,508,308 B2 | 3/2009 | Chung |
| 7,513,425 B2 | 4/2009 | Chung |
| 7,541,933 B2 | 6/2009 | Volpi et al. |
| 7,557,710 B2 | 7/2009 | Sanchez et al. |
| 7,644,016 B2 | 1/2010 | Nycz et al. |
| 7,663,076 B2 | 2/2010 | Tarry |
| 7,770,473 B2 | 8/2010 | Von Lilienfeld-Toal et al. |
| 7,795,491 B2 | 9/2010 | Stewart et al. |
| 7,876,097 B2 | 1/2011 | Greim |
| 7,909,861 B2 | 3/2011 | Balachandran et al. |
| 7,937,789 B2 | 5/2011 | Feher |
| 8,181,860 B2 | 5/2012 | Fleck et al. |
| 8,193,938 B2 | 6/2012 | Halberthal et al. |
| 8,256,674 B2 | 9/2012 | Fleck et al. |
| 8,264,342 B2 * | 9/2012 | Blair .................... A61G 13/10 |
| | | | 340/539.12 |
| 8,323,189 B2 | 12/2012 | Tran et al. |
| 8,358,212 B2 * | 1/2013 | Blair ....................... A61B 5/06 |
| | | | 340/10.1 |
| 8,477,077 B1 | 7/2013 | Nero, Jr. et al. |
| 8,479,989 B2 | 7/2013 | Fleck et al. |
| 8,545,416 B1 | 10/2013 | Kayyali et al. |
| 8,710,957 B2 | 4/2014 | Blair et al. |
| 8,872,662 B2 | 10/2014 | Halberthal et al. |
| 8,878,668 B2 | 11/2014 | Blair et al. |
| 8,937,575 B2 | 1/2015 | Ward et al. |
| 8,985,446 B2 | 3/2015 | Fleck et al. |
| 8,994,358 B2 | 3/2015 | McElhinny et al. |
| 9,317,795 B2 | 4/2016 | Forster |
| 9,414,973 B2 | 8/2016 | Fleck et al. |
| 9,672,397 B2 | 6/2017 | Fleck et al. |
| 2001/0030610 A1 | 10/2001 | Rochelle et al. |
| 2002/0011932 A1 | 1/2002 | Rodgers et al. |
| 2002/0032435 A1 | 3/2002 | Levin |
| 2002/0070863 A1 | 6/2002 | Brooking |
| 2002/0143320 A1 | 10/2002 | Levin |
| 2002/0188259 A1 | 12/2002 | Hickle et al. |
| 2003/0004411 A1 | 1/2003 | Govari et al. |
| 2003/0105394 A1 | 6/2003 | Fabian et al. |
| 2003/0175473 A1 | 9/2003 | Gillum et al. |
| 2004/0030372 A1 | 2/2004 | Ellingboe et al. |
| 2004/0030373 A1 | 2/2004 | Ellingboe et al. |
| 2004/0070399 A1 | 4/2004 | Olsson et al. |
| 2004/0129279 A1 | 7/2004 | Fabian et al. |
| 2004/0137844 A1 | 7/2004 | Desjeux et al. |
| 2004/0250819 A1 | 12/2004 | Blair et al. |
| 2005/0110640 A1 | 5/2005 | Chung |
| 2005/0131397 A1 | 6/2005 | Levin |
| 2005/0154336 A1 | 7/2005 | Kloecker et al. |
| 2005/0247794 A1 | 11/2005 | Jones et al. |
| 2005/0249036 A1 | 11/2005 | Davies et al. |
| 2006/0010607 A1 | 1/2006 | Schneider |

(56) References Cited

U.S. PATENT DOCUMENTS

| | | |
|---|---|---|
| 2006/0052851 A1 | 3/2006 | Anderson et al. |
| 2006/0065060 A1 | 3/2006 | Ito et al. |
| 2006/0106368 A1 | 5/2006 | Miller et al. |
| 2006/0163350 A1 | 7/2006 | Melton et al. |
| 2006/0187044 A1 | 8/2006 | Fabian et al. |
| 2006/0198993 A1 | 9/2006 | Goyarts |
| 2006/0202827 A1 | 9/2006 | Volpi et al. |
| 2006/0212102 A1 | 9/2006 | Frey et al. |
| 2006/0241396 A1 | 10/2006 | Fabian et al. |
| 2006/0241399 A1 | 10/2006 | Fabian |
| 2006/0243720 A1 | 11/2006 | Koch et al. |
| 2006/0271134 A1 | 11/2006 | Frey |
| 2006/0276864 A1 | 12/2006 | Collins |
| 2007/0000605 A1 | 1/2007 | Millette et al. |
| 2007/0004994 A1 | 1/2007 | Sherman |
| 2007/0005141 A1 | 1/2007 | Sherman |
| 2007/0075176 A1 | 4/2007 | Andrews et al. |
| 2007/0109099 A1 | 5/2007 | Raphaeli et al. |
| 2007/0238982 A1 | 10/2007 | Caylor, III |
| 2007/0244532 A1 | 10/2007 | Pierre et al. |
| 2007/0265690 A1 | 11/2007 | Lichtenstein et al. |
| 2007/0281153 A1 | 12/2007 | Yamamoto |
| 2007/0285249 A1 | 12/2007 | Blair et al. |
| 2008/0007411 A1 | 1/2008 | Levin |
| 2008/0018432 A1 | 1/2008 | Volpi et al. |
| 2008/0020189 A1 | 1/2008 | Hofmair et al. |
| 2008/0082092 A1 | 4/2008 | McPherson |
| 2008/0119757 A1 | 5/2008 | Winter |
| 2008/0126122 A1 | 5/2008 | Warner et al. |
| 2008/0161891 A1 | 7/2008 | Pierre et al. |
| 2008/0228248 A1 | 9/2008 | Guyuron et al. |
| 2008/0231452 A1 | 9/2008 | Levin |
| 2008/0244830 A1 | 10/2008 | Davis |
| 2008/0249520 A1 | 10/2008 | Dunning et al. |
| 2008/0249521 A1 | 10/2008 | Dunning et al. |
| 2008/0249524 A1 | 10/2008 | Dunning |
| 2008/0272913 A1 | 11/2008 | Barnes et al. |
| 2008/0281190 A1 | 11/2008 | Petcavich et al. |
| 2009/0000614 A1 | 1/2009 | Carrano |
| 2009/0008449 A1 | 1/2009 | Qing et al. |
| 2009/0110022 A1 | 4/2009 | Snyder et al. |
| 2009/0121965 A1 | 5/2009 | Palmade |
| 2009/0132008 A1 | 5/2009 | Snitting et al. |
| 2009/0215405 A1 | 8/2009 | Domokos et al. |
| 2009/0228082 A1 | 9/2009 | Ross, III et al. |
| 2009/0248120 A1 | 10/2009 | Starr et al. |
| 2009/0267765 A1 | 10/2009 | Greene et al. |
| 2010/0057167 A1 | 3/2010 | Evers et al. |
| 2010/0057170 A1 | 3/2010 | Robinson et al. |
| 2010/0109848 A1 | 5/2010 | Blair et al. |
| 2010/0137704 A1 | 6/2010 | Vij et al. |
| 2010/0198320 A1 | 8/2010 | Pierre et al. |
| 2010/0204763 A1 | 8/2010 | Augustine et al. |
| 2010/0211138 A1 | 8/2010 | Pierre et al. |
| 2010/0211139 A1 | 8/2010 | Pierre et al. |
| 2010/0211141 A1 | 8/2010 | Pierre et al. |
| 2010/0241073 A1 | 9/2010 | Andersen et al. |
| 2010/0324433 A1 | 12/2010 | Wilson et al. |
| 2011/0004276 A1 | 1/2011 | Blair et al. |
| 2011/0056017 A1 | 3/2011 | Schreiber et al. |
| 2011/0098794 A1 | 4/2011 | Anderson et al. |
| 2011/0181394 A1 | 7/2011 | Blair |
| 2015/0054625 A1 | 2/2015 | Blair et al. |
| 2015/0164603 A1 | 6/2015 | Fleck et al. |
| 2015/0216610 A1 | 8/2015 | Augustine |
| 2015/0272688 A1 | 10/2015 | Blair et al. |
| 2016/0070942 A1 | 3/2016 | Dor et al. |
| 2016/0157957 A1 | 6/2016 | Blair |
| 2016/0259954 A1 | 9/2016 | Buhler et al. |
| 2016/0294040 A1 | 10/2016 | Blair |
| 2017/0348172 A1 | 12/2017 | Blair et al. |

FOREIGN PATENT DOCUMENTS

| | | |
|---|---|---|
| CN | 101460096 A | 6/2009 |
| EP | 2 087 850 A2 | 8/2009 |
| JP | 2009539478 A | 11/2009 |
| WO | 02/39917 A1 | 5/2002 |
| WO | 03/073934 A1 | 9/2003 |
| WO | 2004/054801 A1 | 7/2004 |
| WO | 2004/078039 A1 | 9/2004 |
| WO | 2004/086997 A1 | 10/2004 |
| WO | 2007/024348 A2 | 3/2007 |
| WO | 2007/146091 A1 | 12/2007 |
| WO | 2008/008449 A2 | 1/2008 |
| WO | 2008/112709 A1 | 9/2008 |
| WO | 2008/133634 A1 | 11/2008 |
| WO | 2009/151946 A1 | 12/2009 |
| WO | 2009/154987 A1 | 12/2009 |
| WO | 2012/125916 A2 | 9/2012 |

OTHER PUBLICATIONS

Black, "Method and Apparatus to Account for Transponder Tagged Objects Used During Clinical Procedures, Employing a Trocar," U.S. Appl. No. 62/378,515, filed Aug. 23, 2016, 103 pages.

Blair et al., "Mat Based Antenna System to Detect Transponder Tagged Objects, for Example During Medical Procedures," U.S. Appl. No. 13/422,192, filed Mar. 16, 2012, 38 pages.

Blair et al., "Transponder Housing and Device to Mark Implements, Such as Surgical Implements, and Method of Using Same," U.S. Appl. No. 60/894,435, filed Mar. 12, 2007, 30 pages.

Blair, "Apparatus, Method, and Article for Detection and Identification of Multi-Mode Integral Transponder Tagged Objects," U.S. Appl. No. 61/056,229, filed May 27, 2008, 38 pages.

Blair, "Transponder Device to Mark Implements, Such as Surgical Implements, and Method of Manufacturing and Using Same," U.S. Appl. No. 61/086,727, filed Aug. 6, 2008, 30 pages.

Barnes et al., "Method, Apparatus and Article for Detection of Transponder Tagged Objects, for Example During Surgery," U.S. Appl. No. 61/091,667, filed Aug. 25, 2008, 76 pages.

Blair, "Multi-Modal Transponder and Method and Apparatus to Detect Same," U.S. Appl. No. 61/102,749, filed Oct. 3, 2008, 48 pages.

Blair et al., "Method and Apparatus to Detect Transponder Tagged Objects, for Example During Surgery," U.S. Appl. No. 61/109,104, filed Oct. 28, 2008, 73 pages.

Blair, "Detectable Surgical Objects and Methods of Making Same," U.S. Appl. No. 61/109,142, filed Oct. 28, 2008, 47 pages.

Blair, "Transponder Device to Mark Implements, Such as Surgical Implements, and Method of Manufacturing and Using Same," U.S. Appl. No. 61/220,452, filed Jun. 25, 2009, 46 pages.

Blair et al., "Method and Apparatus to Detect Transponder Tagged Objects, for Example During Surgery," U.S. Appl. No. 61/222,443, filed Jul. 1, 2009, 95 pages.

Blair et al., "Method and Apparatus to Detect Transponder Tagged Objects and to Communicate With Medical Telemetry Devices, for Example During Surgery," U.S. Appl. No. 61/222,847, filed Jul. 2, 2009, 122 pages.

Blair, "Transponder Device to Mark Implements, Such as Surgical Implements, and Method of Manufacturing and Using Same," U.S. Appl. No. 61/224,323, filed Jul. 9, 2009, 57 pages.

Blair et al., "Method and Apparatus to Detect Transponder Tagged Objects and to Communicate With Medical Telemetry Devices, for Example During Medical Procedures," U.S. Appl. No. 61/242,699, filed Sep. 15, 2009, 158 pages.

Blair et al., "Method and Apparatus to Detect Transponder Tagged Objects, for Example During Medical Procedures," U.S. Appl. No. 61/242,704, filed Sep. 15, 2009, 127 pages.

Blair, "Method and Apparatus to Account for Transponder Tagged Objects Used During Medical Procedures," U.S. Appl. No. 61/263,726, filed Nov. 23, 2009, 78 pages.

Blair et al., "Mat Based Antenna System to Detect Transponder Tagged Objects, for Example During Medical Procedures," U.S. Appl. No. 61/453,846, filed Mar. 17, 2011, 38 pages.

(56) References Cited

OTHER PUBLICATIONS

Clearcount Medical Solutions, "The SmartSponge System," Downloaded from http://clearcount.com on Oct. 20, 2009, 7 pages.
Extended European Search Report, dated Aug. 18, 2016, for corresponding European Application No. 16163825.9, 15 pages.
Giancoli, "Table of Resistivity," dated Mar. 14, 2014, retrieved from http://moodle1315.up.pt/pluginfile.php/167990/mod_resource/content/1/Resistivity%20and%20Temperature%20Coefficient%20at%2020%20C%20.pdf on Jul. 27, 2016, 1 page.
Hansen et al., "Method and Apparatus to Account for Transponder Tagged Objects Used During Clinical Procedures, Employing a Shielded Receptacle," U.S. Appl. No. 62/360,864, filed Jul. 11, 2016, 99 pages.
Hansen et al., "Method and Apparatus to Account for Transponder Tagged Objects Used During Clinical Procedures Employing a Shielded Receptacle With Antenna," U.S. Appl. No. 62/360,866, filed Jul. 11, 2016, 154 pages.
Inditherm, Inditherm Medical, URL=http://www.inditherm.com/default.asp?chapterid=4&langid=1, download date Jun. 9, 2011.
Inditherm, Patient Warming—Technology, URL=http://www.inditherm.com/default.asp?ContentID=70, download date Jun. 9, 2011.
Inditherm, SpeedHeat—Features and Benefits, URL=http://www.inditherm.com/default.asp?contentid=75, download date Jun. 9, 2011.
Poirier et al., "Method and Apparatus to Account for Transponder Tagged Objects Used During Clinical Procedures, for Example Including Count in and/or Count Out and Presence Detection," U.S. Appl. No. 62/360,868, filed Jul. 11, 2016, 113 pages.
Poirier et al., "Method and Apparatus to Account for Transponder Tagged Objects Used During Clinical Procedures, for Example Including Count in and/or Count Out and Presence Detection," U.S. Appl. No. 62/378,511, filed Aug. 23, 2016, 114 pages.
Blair et al., "Method and Apparatus to Detect Transponder Tagged Objects and to Communicate With Medical Telemetry Devices, for Example During Medical Procedures," U.S. Appl. No. 15/786,001, filed Oct. 17, 2017, 160 pages.
Extended European Search Report, dated Jul. 30, 2015, for European Application No. 14176398.7, 7 pages.
Inditherm, Therapeutic Heating (SpeedHeat), URL=http://www.inditherm.com/default.asp?contentid=74, download date Jun. 9, 2011, 2 pages.
International Search Report, dated Dec. 23, 2014, for PCT/US2014/045942, 3 pages.
Written Opinion, dated Dec. 23, 2014, for PCT/US2014/045942, 7 pages.
Extended European Search Report dated Jun. 24, 2016, for corresponding EP Application No. 16151391.6-1659, 8 pages.

* cited by examiner

MAT BASED ANTENNA AND HEATER SYSTEM, FOR USE DURING MEDICAL PROCEDURES

CROSS-REFERENCE TO RELATED APPLICATIONS

This application claims the benefit of and priority to U.S. Provisional Patent Application No. 62/143,726 filed Apr. 6, 2015, the entire disclosure of which is incorporated by reference herein.

BACKGROUND

Technical Field

This disclosure generally relates to devices useful during medical procedures, which include the detection of the presence or absence of objects tagged with wireless transponders and/or reading information from and/or writing information to transponders, which may, for example, allow the detection of retained medical supplies during medical procedures, for instance surgical or labor and delivery procedures.

Description of the Related Art

It is often useful or important to be able to determine the presence or absence of an object.

For example, it is important to determine whether objects associated with a medical procedure, for instance a surgery or child birth deliveries, are present in a patient's body before completion of the medical procedure. Such objects may take a variety of forms used in medical procedures. For example, the objects may take the form of instruments, for instance scalpels, scissors, forceps, hemostats, and/or clamps. Also for example, the objects may take the form of related accessories and/or disposable objects, for instance sponges, gauzes, and/or absorbent pads. When used in surgery, failure to locate an object before closing the patient may require additional surgery, and in some instances may have serious adverse medical consequences. In other medical procedures, such as vaginal child birth deliveries, failure to remove objects, for instance gauze or absorbent pads can lead to infections.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Some facilities may wish to install a single interrogation and detection system in each surgery theater or room in which medical procedures are conducted, while other facilities may move an interrogation and detection system between multiple surgical theaters or other rooms. In either case, the overall system will require a large number of transponders, since at least one transponder is carried, attached or otherwise coupled to each object which may or will be introduced into a patient or subject during the medical procedure. Consequently, the transponders should be inexpensive. However, inexpensive transponders typically have a relatively large variation in the frequency of signals they emit, making it difficult to accurately detect the signals returned by the transponders. This may be particularly difficult in some environments which are noisy with respect to the particular resonant frequencies of the transponders. Rooms in hospitals in which medical procedures are performed tend to have increasingly larger amounts of electronic equipment, and hence are becoming notoriously noisy environments.

Further, it may be advantageous to read information from transponders, for instance unique identifiers which uniquely identify the transponder, and which may be used to identify an object to which the transponder is physically coupled. It may additionally or alternatively be advantageous to write information to transponders and/or send commands or instructions for the transponders to execute. Transponders known as radio frequency identification (RFID) transponders or "tags" may be used to store information, such as a unique identifier, which may be read wirelessly. Some RFID transponders are active transponders, having a discrete consumable power source such as a chemical battery. Other RFID transponders are passive transponders, deriving power from an interrogation signal transmitted by an RFID interrogator or reader. Some RFID transponders are read only. Other RFID transponders are writable, capable of storing information transmitted to the transponder.

While transponder based systems may provide numerous benefits, particularly in the medical field, the adoption of such is likely to be enhanced by providing solutions which are highly accurate (i.e., no false negatives and/or no false positives) and simple to operate. Medical care providers are typically busy, and requiring additional training and increasing their workload will discourage adoption of transponder based systems. Consequently, new approaches to detection of the presence and absence of transponder and/or communications therewith are highly desirable.

BRIEF SUMMARY

A mat-based multi-antenna and heater system may advantageously allow automatic interrogation of a field which encompasses all or a portion of a body of a patient, without the need for medical personnel to manually scan the field, while selectively providing warmth to the patient.

Automated interrogation may reduce the effort required by medical personnel, who are often very busy during medical procedures, simplifying their tasks. Such may also reduce the amount of extra training required by medical personnel, reducing costs. Such may also advantageously produce a more complete scan of the entire field, thereby increasing the accuracy of interrogation by reducing the possibility of false positives or false negatives. In the case of false negatives, such may eliminate or reduce post-procedure infections, which often leads to unnecessary pain, lost time, and increased costs, as well as potential exposure to malpractice or personal injury claims. Such may also eliminate or reduce the need for follow up procedures to remove or retrieve retained objects, reducing risks to a patient and saving significant amounts of time and money associated with the follow up procedures. In the case of false positives, such may eliminate or reduce the time spent by medical personnel in attempting to locate an object which was not really retained. Such may also reduce risks associated with delaying the end of the procedure (e.g., closing an incision).

Selective heating of the patient may advantageously keep a patient from unintentionally entering in to a shock state, which is often at least partially contributable to a loss of body heat and reduction in the body core temperature.

To be useful, a mat-based antenna and heater system should be able to withstand environmental and handling conditions to which the mat-based antenna system will be subjected during use in the medical facility. Such may include the ability to withstand various types of sterilization, disinfection or other sanitization procedures which may employ exposure to high temperatures and/or pressures, exposure to harsh chemicals and/or to various wavelengths of electromagnetic energy. Such may also include the ability to be manipulated including being laid upon an appropriate patient support structure and withstanding movement of a patient.

A mat based antenna and heater system for use in detecting transponder tagged objects which are used in performing medical procedures may be summarized as including a first sheet of an electrically insulative material that is sized to support at least a portion of a patient, the first sheet having an upper face and a lower face opposed to the upper face; a plurality of antennas positioned successively along at least a portion of a length of the first sheet; a first layer of silicon carried by the upper face of the first sheet; a second layer of silicon carried by the lower second face of the first sheet; a gel layer positioned relatively above the first layer of silicon with respect to the first sheet; and a foam layer spaced relatively above the gel layer with respect to the first sheet.

The mat based antenna and heater system may further include a top cover sheet spaced relatively above the foam layer with respect to the first sheet. The top cover may be a nylon polyurethane laminate.

The mat based antenna and heater system may further include a bottom cover sheet spaced relatively below the second layer of silicon with respect to the first sheet. The bottom cover may be a non-slip fabric.

The mat based antenna and heater system may further include a thermoplastic polyurethane positioned between the first layer of silicon and the gel layer. The first sheet may be a polyethylene film. The antennas may be traces of metal carried by the polyethylene film and the traces may have dimensions that make the antennas radiolucent. The polyethylene film and the first and the second silicon layers may form a unitary laminate structure. The antennas may each include a respective stripe-line aluminum coil having a number of windings, each stripe-line aluminum coil having a thickness that is not greater than 200 microns. Each stripe-line aluminum coil may have a thickness that is not greater than 100 microns. The foam layer may be a polyurethane foam. The gel layer may be a thermoplastic elastomer. The antennas may include a first set of three coil antennas spaced along the length of the first sheet, and a second set of three coil antennas spaced along the length of the first sheet, the second set of antennas spaced laterally across a width of the first sheet from the first set of antennas.

The mat based antenna and heater system may further include at least one cable interface head to allow selective communicative coupling of the antennas with a controller. The at least one cable interface head may include an upper foam member, a lower foam member, and a plurality of wires, each of the wires including an electrically insulative sheath along at least a portion thereof, the wires protectively sandwiched between the upper and the lower foam members. The at least one cable interface head may further include a housing bottom and a housing cover, the housing cover physically coupled to the housing bottom, the upper and the lower foam members sandwiched between the physically coupled housing bottom and cover. The at least one cable interface head may further include an upper layer of an electrically insulative tape positioned between the upper foam member and a lower layer of an electrically insulative tape positioned between the lower foam member and the housing bottom. The at least one cable interface head may further include a soft epoxy member and a hard epoxy member positioned opposed to one another proximate a location where the wires are electrically coupled to a number of conductive traces carried by the first sheet of electrically conductive material.

The mat based antenna and heater system may further include a cable carrying the plurality of wires; and an interface head having a housing bottom, a housing cover, and a plurality of communicative paths extending therethrough, the communicative paths communicatively coupling the antennas of the mat based antenna and heater system and the wires of the cable.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
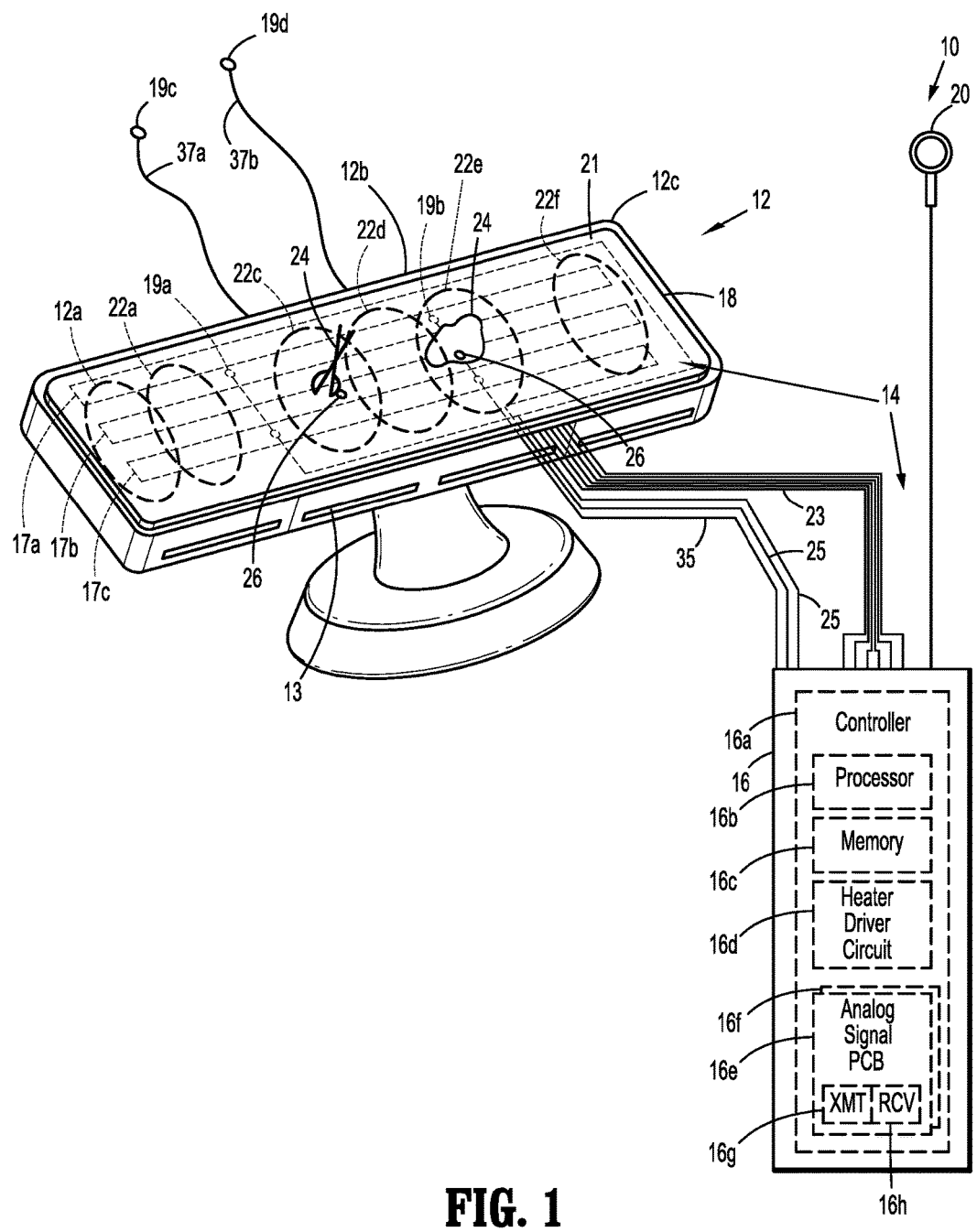
FIG. 1 is a schematic diagram showing an environment in which a medical procedure is performed, for example a surgical environment including a table, bed or other structure to carry or support at least a portion of a patient, that includes a plurality of antennas and a heater or heating element, and a controller communicatively coupled to the antennas and heater, which implements an interrogation and detection system to detect an object tagged with a transponder in a patient, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Further more, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Many of the embodiments described herein, perform interrogation and detection of transponder tagged objects using multiple antennas (e.g., six antennas). Successive ones of the antennas may be used to transmit an interrogation signal, while two or more antennas are monitored for a response to the interrogation signal. Such may provide significant advantages over more conventional methods, for example motion based methods that employ motion (e.g., sweeping) of an antenna (e.g., wand) over a patient. For instance, this allows the transmit and receive paths to the transponder to be different from one another (e.g., transmit path is from a first antenna to a transponder, while the receive path is from the transponder to a second antenna). Hence, the path length to the transponder may be shortened in many configurations, thus improving the signal. For instance, when using a single antenna to both transmit an interrogation signal and to receive a response to the interrogation signal, the power of the received signal is equal to about the $6^{th}$ root of the input power. However, when using multiple antennas to transmit and receive over the same area, interrogation path length in one direction may be shorter. Another advantage is that all scan time is averaged, allowing a longer noise time averaging (e.g., 10 seconds) as opposed to motion based scanning, where integration time may be limited (e.g., about 0.25 seconds per sample). Even further, a representative value of noise samples measured over a plurality of antennas may be employed to determine noise to be removed from noise plus signals received at one of the antennas, thereby advantageously lowering a noise floor and/or increasing range or performance. Thus, the various disclosed embodiments may provide significantly better performance.

Figure 2:
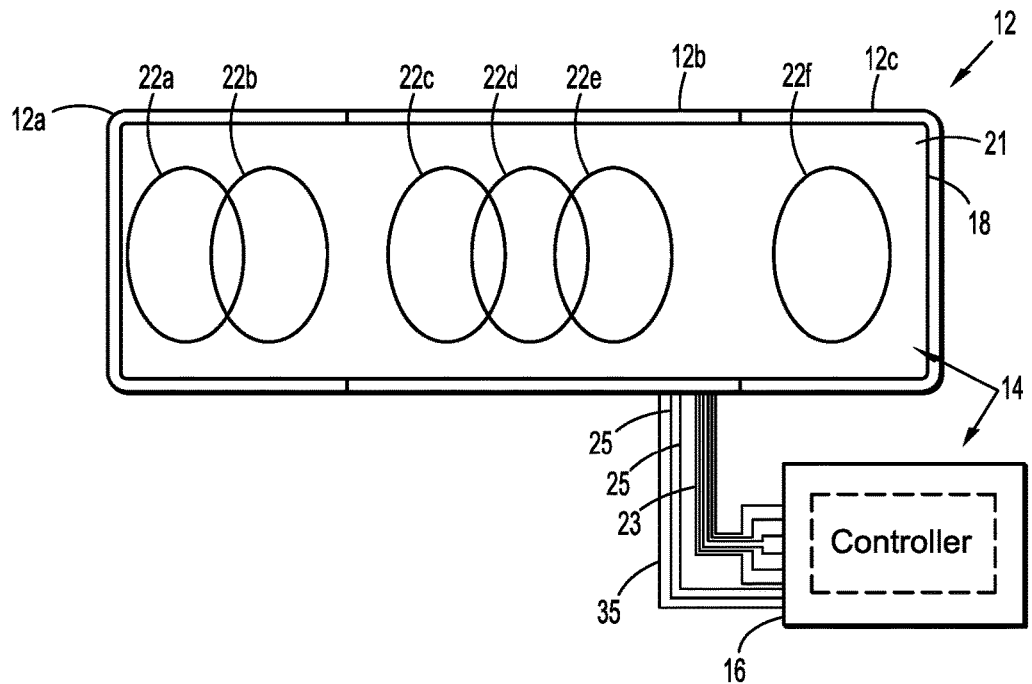
FIG. 2 is a top plan view of the mat based antenna and heater system and controller of FIG. 1.
Figure 3:
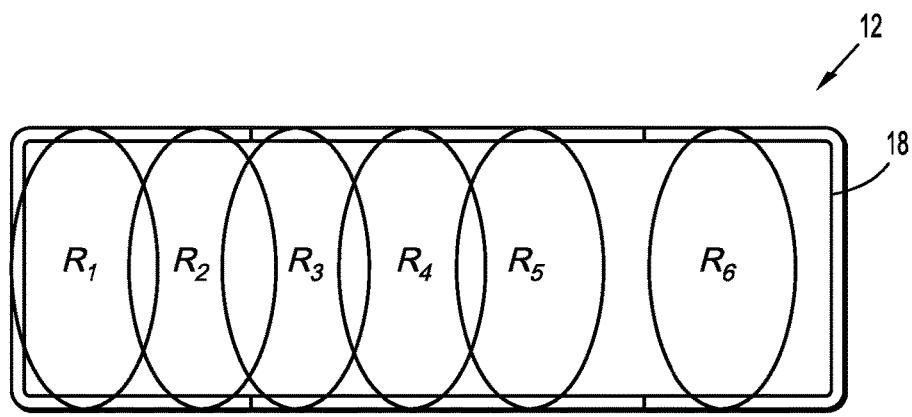
FIG. 3 is a top plan view of the mat based antenna and heater system of FIG. 1 depicting exemplary ranges of respective antennas.

FIGS. 1-3 show a medical procedure environment 10 in which medical procedures are performed, for example a surgical environment in which surgeries are performed, a delivery room in which child birth deliveries are performed, an examination room, patient room or a physician's office in which examinations, minor diagnostic and/or therapeutic procedures or other medical procedures are performed.

The medical procedure environment 10 includes a structure 12 on which a patient may sit, lie or otherwise be supported in whole or in part, which is denominated herein as patient support structure 12. The patient support structure 12 may for instance, take the form of a table (e.g., surgical table), bed, or other structure 12 which can carry a patient or portion thereof. The patient support structure 12 may have dimensions sufficient to support at least a portion of a patient during a medical procedure, for instance during surgery, child birth, examination, treatment, etc. Hence, the patient support structure 12 may, for example, have a length of over six feet and a width of over two feet. The patient support structure 12 may have two or more articulated sections 12a-12c, as illustrated in FIG. 1, or may be an unarticulated structure.

The patient support structure 12 is preferably made of a rigid material. The patient support structure 12 is preferably radiolucent, and may include one or more slots or receptacles 13 (only one called out in FIG. 1) to removably receive film, for instance X-ray film. Various radiolucent materials may be employed, for instance carbon fiber or radiolucent plastics. Such advantageously allows various imaging techniques to be employed, for instance X-ray imaging. The patient support structure 12 may, for example, be molded from plastics such as an acrylic or a phenolic resin (e.g., commercially available under the trademark SPAULDITE®). The patient support structure 26 may, optionally, include a frame. The frame may be made of a metal, which typically would not be radiolucent. In such embodiments, the frame preferably makes up a small percentage of the total area of the patient support structure 12 and is spaced so as to not occlude an imaging system's field-of-view of the patient when the patient is supported by the patient support structure 12.

The patient support structure 12 may be capable of withstanding multiple cycles of sterilization (e.g., chemical, heat, radiation, etc.). A large variety of surgical tables, patient beds, delivery beds, and other structures capable of carrying a patient or a portion of a patient are commercially available. Many of these commercially available structures include electric motors and electronics. Typically, there is no or minimum regulation of non-ionizing electromagnetic radiation generated by such electric motors and electronics. Hence, many environments 10 in which medical procedures are performed tend to be electromagnetically noisy environments.

The medical procedure environment 10 includes an interrogation and detection system 14. The interrogation and detection system 14 includes a console 16 and a mat based antenna and heater system 18 communicatively coupled to the console 16. The interrogation and detection system 14 optionally includes a moveable antenna, for example a set of coils in the form of a hand-held wand 20.

The console 16 may include an interrogation and detection system interface. The interrogation and detection system interface may include one or more ports (e.g., communications ports) that allow communicative coupling to be selectively or detachably made between the controller of the console 16 and the antennas 22. The interrogation and detection system interface may include one or more ports (e.g., electrical plugs and/or sockets, communications ports) that allow coupling to be selectively or detachably made between the controller of the console 16 and one or more heaters or heating elements 17a, 17b, 17c (collectively 17)

and/or one or more temperature responsive or indicative sensors 19a, 19b (four shown, only two called out in FIG. 1, collectively 19) of the mat based antenna and heater system 18. Such ports may, for example, take the form of coaxial connectors, other communications connectors, electrical plugs and/or sockets.

Interrogation and detection system console 16 may include one or more output devices to provide indications to a user. For instance, the console 16 may include one or more visual indicators to provide indications of a presence and/or an absence of an object. Such may also provide a visual indication that is indicative of a status of a scanning operation by the interrogation and detection system 14, for instance scanning started, scanning completed, and/or occurrence of an error condition. Such may also provide a visual indication that is indicative of a status of a scanning operation by the interrogation and detection system 14, for instance scanning started, scanning completed, and/or occurrence of an error condition. Also for instance, the console 16 may include one or more visual indicators to provide indications of a temperature (e.g., degrees Centigrade or degrees Fahrenheit) at least proximate a patient and/or an indication of which portion or state of a temperature cycle the heater is currently operating in, (e.g., heating, not heating, warming up, cooling down, steady state heating).

The visual indicators may take a variety of forms, for example light sources of one or more colors. Light sources may include incandescent lights, light emitting diodes (LEDs), organic light emitting diodes (OLEDs), and/or liquid crystal displays (LCDs). Also for instance, console 16 may include one or more aural indicators to provide aural indications of a presence and/or an absence of an object and/or a status of a scan operation or occurrence of an error condition. The aural indicator may, for example, take the form of one or more speakers. The console 16 may include one or more switches that allow input to be provided to the controller. Switches may, for example, allow a user to turn ON the interrogation and detection system 14, start a scan operation, stop a scan operation, adjust a sensitivity of the scanning, adjust one or more frequencies, select or adjust an output type (e.g., type of visual alert, type of aural alert) or level (e.g., brightness, sound level or volume, etc.). Switches or other input devices may, for example, allow a user to set a desired temperature to be maintained, or set a desired heating pattern to be executed by the console, or to set a set point or threshold in a temperature feedback loop executed by the console.

The mat based antenna and heater system 18 may be removably located on the patient support structure 12. For example, the mat based antenna and heater system 18 may be detachably secured to the patient support structure 12 via various fasteners, for instance ties, or hook and loop fastener commonly available under the trademark VELCRO®. Alternatively, the mat based antenna and heater system 18, or portion thereof, may rest unsecured upon a surface of the patient support structure.

The mat based antenna and heater system 18 includes one or more mats 21 and a plurality of antennas 22a-22f (collectively 22, shown in broken line in FIG. 1 to indicate that such are hidden in that view). The antennas 22 may be distributed successively along a length of the mat 21, and may be sufficiently wide to provide wireless communications coverage over a width (e.g., 35 inches, 37 inches, 39 inches) of the mat 21. The antennas 22 may be communicatively coupled to the console 16, for example via a wired communications path such as one or more cables 23 (e.g., coaxial cable).

The mat based antenna and heater system 18 includes one or more heaters or heating elements 17. The heaters or heating elements 17 may take a variety of forms. For example, the heaters or heating elements 17 may take the form of conductive elements (e.g., wires, traces, foils) which produce heat as a current passes through the conductive element(s). The conductive element(s) may comprise carbon fiber, or other conductive materials, including metallized inks, nickel-chromium alloys (e.g., 80% nickel, 20% chromium), cupronickel alloys (CuNi), Kanthal alloys (FeCrAl), etched foils, ceramic heating elements (e.g., molybdenum disilicide, PCT ceramic elements), silicone rubber insulated heater wire, polyimide film insulated heaters, stainless steel resistor elements. The heaters or heating elements 17 may dissipate approximately 0.2-0.5 watts/square inch. The heaters or heating elements 17 may have a resistivity of at least approximately 49 micro-ohms·cm at 20° C. or 1.25 ohms mm$^2$/m at 20° C. This may be substantially more than a resistivity of the antennas 22 (e.g., 25%, 100%, 200%, 10 times more). The heaters or heating elements 17 may be electrically coupled to the console 16, for example via a wired path such as one or more cables 25 (e.g., coaxial cable).

The mat based antenna and heater system 18 optionally includes one or more temperature responsive or indicative sensors 19a-19d (six illustrated four called out in FIG. 1, collectively 19). Some or all of the temperature sensors 19a, 19b may be integral with the mat. These integral sensors 19a, 19b may, for instance, allow the temperature proximate a portion (e.g., back) of a patient to be sensed during a medical procedure. Some or all of the temperature sensors 19c, 19d may be separate and distinct from the mat. These separate and distinct sensors 19a, 19b may, for instance, allow the temperature proximate another portion (e.g., front) of a patient to be sensed during a medical procedure, and may include a gel layer and/or foam layer similar in construction to the mat. The temperature responsive or indicative sensors 19 may take a variety of forms. For example, the temperature responsive or indicative sensors 19 may take the form of one or more thermistors (e.g., surface mount chip thermistor commercially available from Panasonic as part ERT-J1VG103FA), thermocouples, resistance thermometer, silicon bandgap temperature sensor. Particularly where integral with the mat, the temperature responsive or indicative sensors 19 may, for example, be responsive to an amount of current being passed through one or more heaters or heating elements 17, for instance measuring the electrical current and/or voltage as an indication of the heat being produced by the heaters or heating elements 17. The integral sensors 19a, 19b may be communicatively coupled to the console 16, for example via a wired path such as one or more cables 35 (e.g., coaxial cable). The separate and distinct sensors 19c, 19d may be communicatively coupled to the console 16 via the mat, for example via respective first wired paths such as one or more cables 37a, 37b (two illustrated in FIG. 1, collectively 37) (e.g., coaxial cable) and a second wired path such as one or more cables 35 (e.g., coaxial cable). Wiring between the mat and the console 16 may be commonly bundled, for instance as illustrated by reference numbers 23, 25, 35.

As illustrated in FIG. 3, each antenna 22a-22f has an associated range $R_1$-$R_6$, respectively. The magnitude of the ranges $R_1$-$R_6$ may be dependent on the shape or type of antenna 22a-22f, the power provided via a transmitter, and/or sensitivity of a receiver, as well as other factors such as background noise or multi-path interference. The magnitude of the various ranges $R_1$-$R_6$ may be identical to one another, or may vary from one another. The ranges $R_1$-$R_6$ along with the positioning of the antennas 22a-22f relative to one another, and hence the positioning of the ranges $R_1$-$R_6$ with respect to one another, should be sufficient to encompass an entire body or portion thereof which will be subjected to automated scanning, without any gaps or missed portions.

The console 16 may take any of a variety of forms which includes a wireless transmitter, receiver or transceiver, and suitable control subsystem configured or configurable to wirelessly transmit interrogation signals, receive response signals to the interrogation signals, and preferably process information associated with response signals. The transmitter, receiver or transceiver will typically operate in the radio and/or microwave portions of the electromagnetic spectrum. Processing response signals may, for instance include simply determining whether a response signal was received or not, and/or reading or otherwise determining information encoded in the response signals. As used herein and in the claims, the term "signals" and variations thereof (e.g., signal) refers to communications or transmission of energy, whether information is encoded therein or not.

The console 16 may also provide signals and/or current to the heaters or heating elements 17, to cause the heaters or heating elements 17 to generate heat. For example, the console 16 may include dedicated heater driver circuitry 16d that selective provides current to the heaters or heating elements 17, for example under control of a controller 16a. The controller 16a may include a processor 16b and non-transitory computer- or processor-readable medium such as memory 16c. The heaters or heating elements 17 may be selectively adjustable to produce a desired temperature, for example by modulating current supplied to the heaters or heating elements 17 for instance according to a pulse width modulated drive signal. In some implementations, the console 16 may also receive temperature indicative signals from the sensors 19, and process the received temperature indicative signals to determine at least an approximation of a temperature at least proximate some portion of the patient or mat. The console may use the received temperature indicative signals as feedback, adjusting a current supplied to the heaters or heating elements 17 to maintain one or more portions of the mat at a desired temperature or desired temperatures. Thus, the console may compare sensed temperatures or values indicative of temperatures to one or more desired temperature set points, and increase or decrease current supplied to the heaters or heating elements 17 accordingly. The set points may be manually entered by the user (e.g., medical care provider), or may be automatically or autonomously set based on characteristics of the patient and/or medical procedures to be performed.

Examples of suitable consoles are provide in U.S. patent application Ser. No. 12/606,688 filed Oct. 27, 2009, published as U.S. patent application publication 2010-0109848. In particular, the console 16 may, for example, include two analog signals printed circuit boards 16e, 16f (two shown), each with circuitry including transmitters 16g, receivers 16h or transceivers to handle four (4) channels. The console 16 may, for example, additionally include a digital signals printed circuit board with one or more processors 16b for instance microprocessors (e.g., ATOM™ processor, commercially available from Intel Corporation), digital signal processors, programmable gate arrays (e.g., commercially available from ATMEL Corporation) and/or application specific integrated circuits, configured to digitally process signals received from the antennas 22 via the analog circuit boards. The console 16 may, for example, additionally include one or more nontransitory computer- or processor-readable media such as memory 16c, for instance nonvolatile memory such as read only memory (ROM) or FLASH memory, volatile memory such as random access memory (RAM), or spinning media such as magnetic disks, or optical disks and associated readers. The various components may be communicatively coupled by one or more buses such as power buses, instruction buses, and/or data buses.

As discussed in detail below, the interrogation and detection system 14 is operable to ascertain a presence or absence of objects 24a, 24b (collectively 24) tagged with transponders 26a, 26b (collectively 26), which may be in or on a patient (not shown). Thus, for example, receipt of a response signal to an interrogation signal may indicate a presence of a transponder 26 in a field of interrogation of the interrogation and detection system 14 or an antenna 22 thereof, even where the response signal does not encode any information. Additionally, or alternatively, interrogation and detection system 14 may be operable to read information encoded or stored in the transponders 26, write information to a memory in the transponders 26, and/or send instructions or commands to the transponders 26 for the transponders 26 to execute or perform.

The objects 24 may take a variety of forms, for example instruments, accessories and/or disposable objects useful in performing medical procedures, for example surgical procedures, child birth delivery procedures, and/or other medically related procedures. For instance, some objects 16a may take the form of scalpels, scissors, forceps, hemostats, and/or clamps. Also for example, some objects 22b may take the form of sponges (e.g., surgical sponges), gauze and/or padding. The objects 24 are tagged, carrying, attached or otherwise coupled to a respective transponder 26. Some embodiments of the interrogation and detection system 14 disclosed herein are particularly suited to operate with transponders 26 which are not accurately tuned to a chosen or selected resonant frequency. Consequently, the transponders 26 do not require high manufacturing tolerances or expensive materials, and thus may be inexpensive to manufacture.

Transponders 26 may, for example, include a miniature ferrite rod with a conductive coil wrapped about an exterior surface thereof to form an inductor (L), and a capacitor (C) coupled to the conductive coil to form a series LC circuit. The conductive coil may, for example, take the form of a spiral wound conductive wire with an electrically insulative sheath or sleeve.

The transponders 26 additionally, or alternatively, include one or more radio frequency identification (RFID) transponders. The RFID transponders are preferably passive transponders, but may be active transponders. The RFID transponders preferably store a unique identifier. The RFID transponder may, or may not, be capable of allowing information to be read from the RFID transponder by an interrogator or reader. The RFID transponder may, or may not, be capable of storing information wirelessly sent to the RFID transponder by an interrogator or reader. The RFID transponders may, or may not, be capable of executing various commands. The unique identifier may, for example, allow information to be determined, for example via a lookup table or other data structure. The unique identifier may also allow the RFID transponder to be uniquely addressed with instructions, commands or data to be written to the transponder.

The transponders 26 may include an encapsulation that encapsulates the ferrite rod, conductive coil, and capacitor and/or RFID circuit and antenna. The encapsulant may be a bio-inert plastic, that protects the ferrite rod, conductive coil and/or capacitor from pressure and/or from fluids, for example bodily fluids. In some embodiments, the ferrite rod may include a passage sized to receive a physical coupler, for example a bonding tie or string. The bonding tie or string may take the form of an elastomeric X-ray opaque flexible elongated member, that may be used to attach the transponder 26 to various types of objects 24, for example surgical sponges. The transponder 26 may have a length of about 8 millimeters and a diameter of about 2 millimeters. Employing such small dimensions ensures that the transponder 26 does not impede deformation of objects 16 such as sponges. The transponder 26 may include an optional diode (not shown), to protect against over-voltage occurrences caused by other electronic instruments.

The transponders 24 may be attached to hemostats, scissors, certain forms of forceps, and the like. In some embodiments, the transponders 26 may be coupled to the object 24 by way of a clamp or holder. In some embodiments, the transponders 26 may be retained within a cavity of the holder. In some embodiments, the holder may be fashioned of a durable deformable material, such as surgical grade polymer, which may be deformed to clamp securely onto the finger or thumbhole of an instrument. In other embodiments, the transponders 26 may be attached to objects 24 by way of pouches fashioned of sheet material (e.g., surgical fabric) surrounding the transponder 26. The transponder 26 is retained within the pouch, and in some embodiments the pouch may be sewn or otherwise sealed. Sealing may be done with adhesive, hot glue, clamping, grommets, or the like. Various embodiments of suitable transponders and retention devices are discussed in U.S. Provisional Patent Application No. 60/811,376 filed Jun. 6, 2006, U.S. Provisional Patent Application No. 61/091,667 filed Aug. 25, 2008, U.S. patent application Ser. No. 11/759,141 filed Jun. 6, 2007, U.S. patent application Ser. No. 12/046,396 filed Mar. 11, 2008, U.S. patent application Ser. No. 12/606,688 filed Oct. 27, 2009, U.S. Pat. No. 6,026,818 issued Feb. 22, 2000, U.S. Design patent application Ser. No. 29/322,539 filed Aug. 6, 2008 and U.S. Design Pat. No. D568,186 issued May 6, 2008, all of which are incorporated herein by reference in their entireties.

Figure 4:
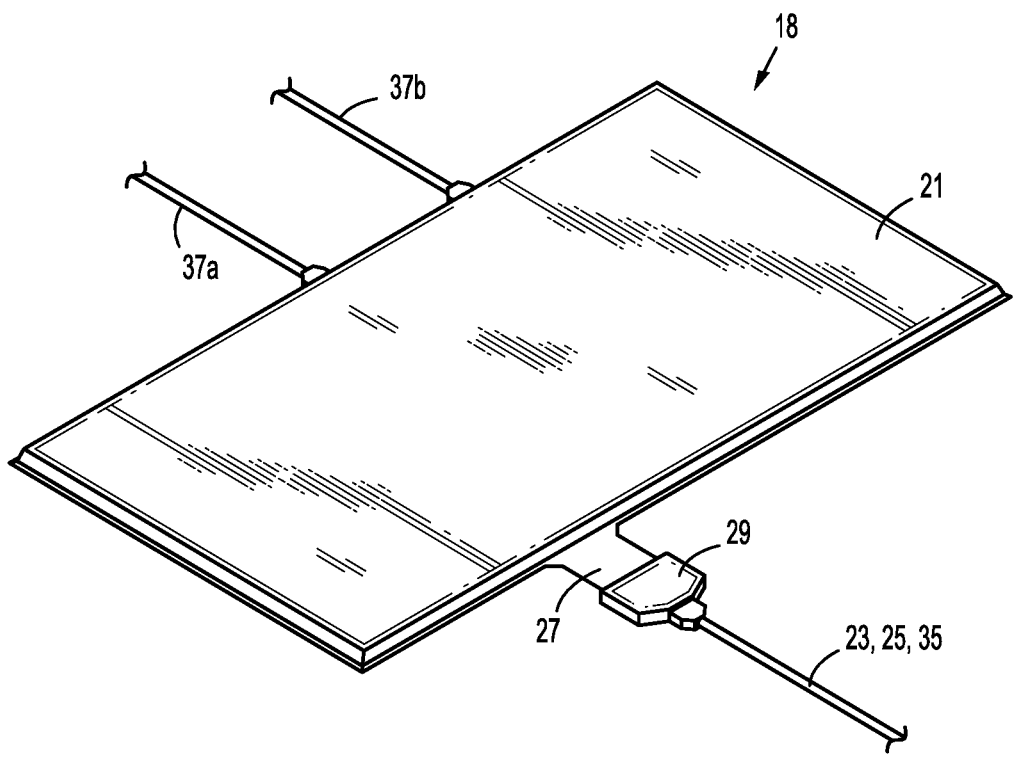
FIG. 4 is an isometric view of the mat based antenna and heater system of FIG. 1, including a cable extending therefrom and cable interface head.
Figure 5:
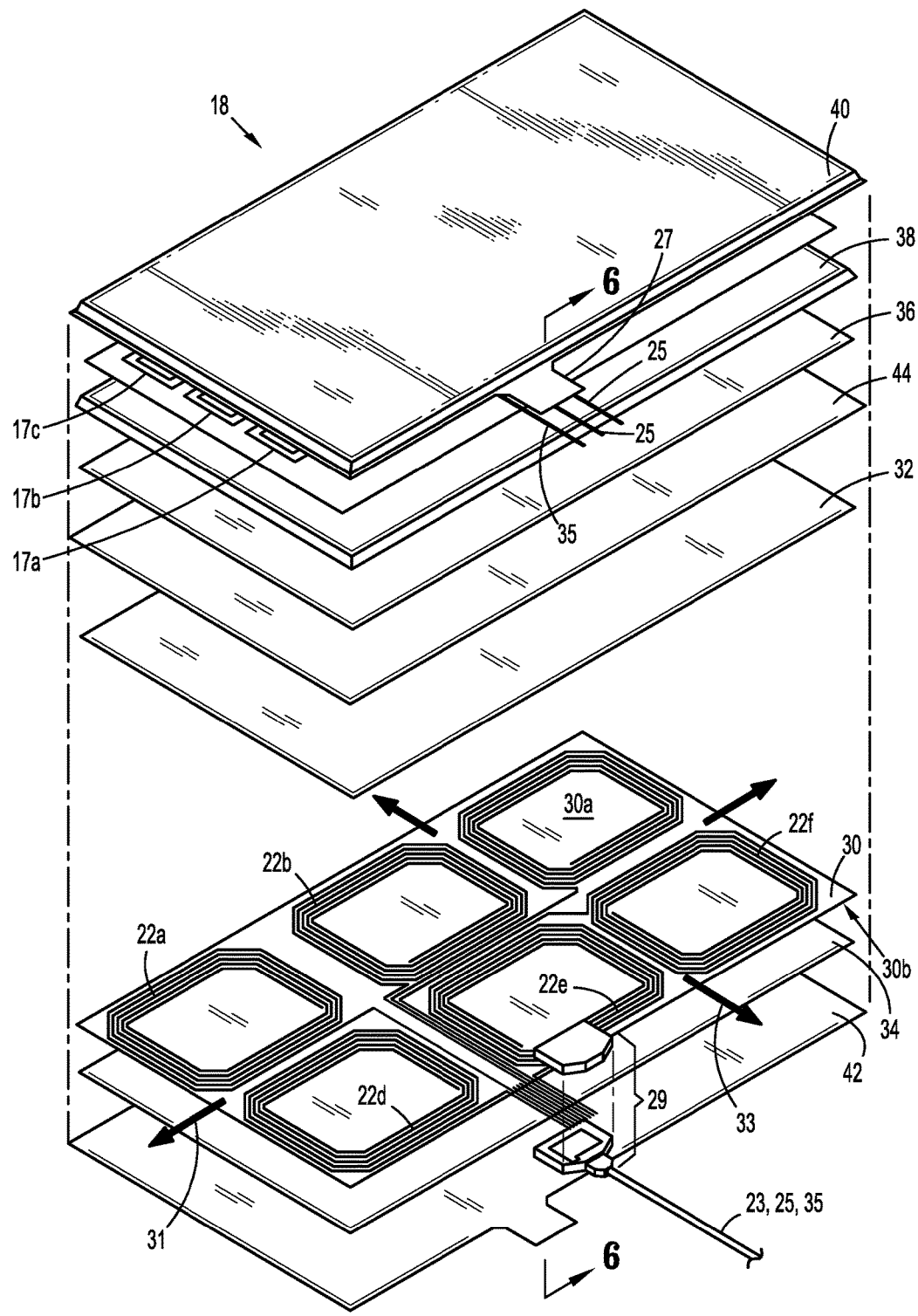
FIG. 5 is an exploded isometric view of the mat based antenna and heater system of FIG. 4.
Figure 6:
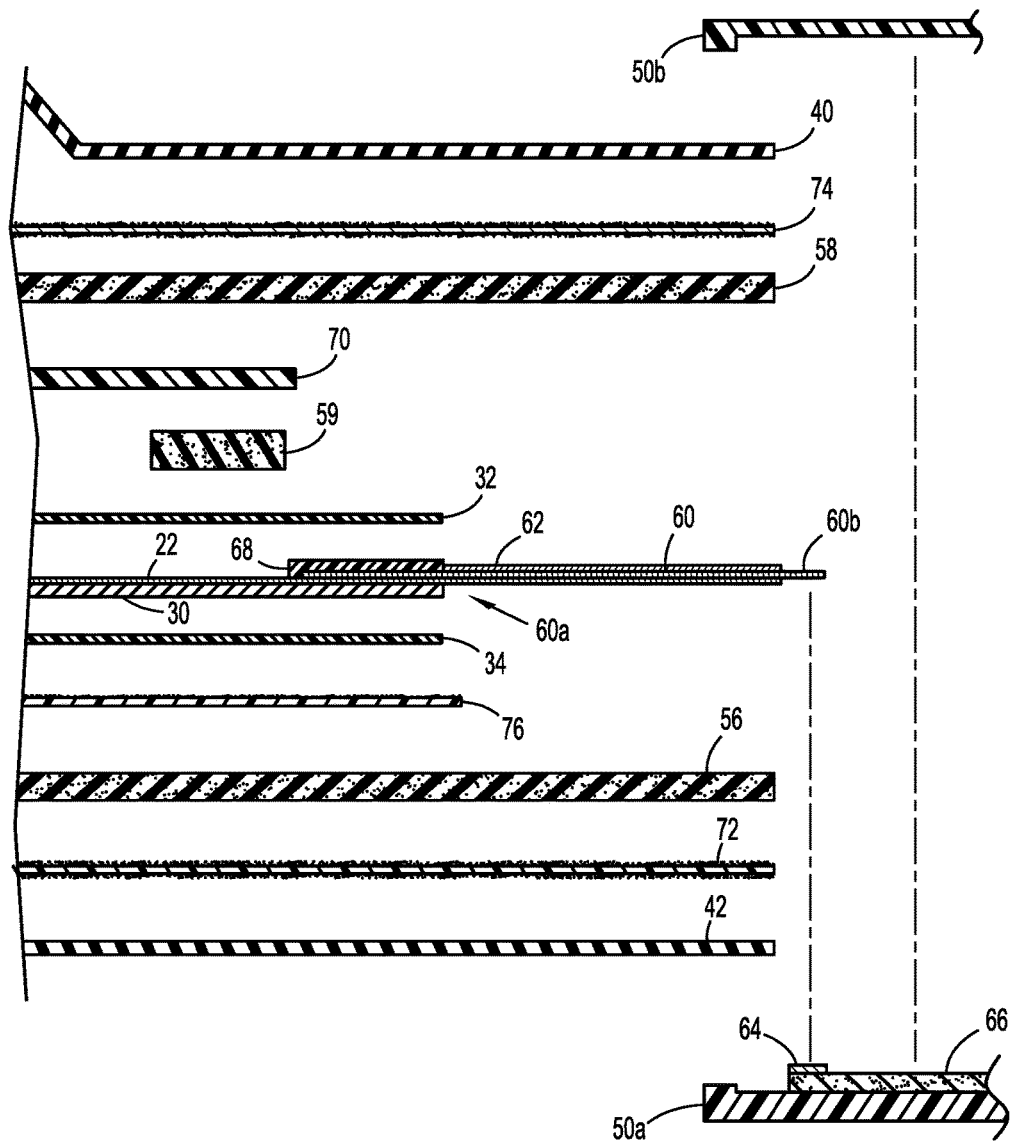
FIG. 6 is an exploded side elevational view of the cable interface head and portion of the mat based antenna system, of FIG. 4.

FIGS. 4-6 show the mat based antenna and heater system 18, according to one illustrated embodiment.

The mat based antenna and heater system 18 includes the mat portion 21 and the plurality of antenna elements 22 carried by the mat portion 21. A tab 27 extends from the mat portion 21, which is physically coupled to a cable interface head 29 of the cable(s) 23, 25, 35. As discussed below, the cable interface head 29 advantageously provides protection to the electrical interface between the antenna elements 22 and the communicative paths (e.g., electrical paths or wires, optical fiber) of the cable(s) 23, 25, 35.

As best illustrated in FIG. 5, the mat portion 21 may include a number of layers of various materials, which provide unique advantages, functionality and results, generally described below.

For example, the mat portion 21 may include a first substrate or sheet 30 of an electrically insulative material. The first substrate or sheet 30 may, for example, take the form of a polyethylene film. The first substrate or sheet 30 may be sized in length and/or width to support at least a portion of a patient. The first substrate or sheet 30 has two outer surfaces, namely an upper face 30a and a lower face 30b opposed to the upper face 30a. The first substrate or sheet 30 may, or may not, take the form of a laminate structure comprised of multiple plies of material.

The antennas 22 may, for example, take the form of one or more traces of an electric conductor or electrically conductive material (e.g., metal) carried by the first substrate or sheet 30. For example, the electric conductor or electrically conductive material may be carried on one of the outer surfaces (e.g., first or second faces 30a, 30b, respectively) of a polyethylene film. Alternatively, the electric conductor or electrically conductive material may be carried on both of the outer surfaces (e.g., first or second faces 30a, 30b, respectively) of the first substrate or sheet 30. Alternatively, or additionally, the electric conductor or electrically conductive material may be carried on an inner surface or layer (not shown) of the first substrate or sheet 30, for example where the first substrate or sheet 30 is a laminate structure. Conductive traces may be formed by silk screen printing, or by other printing or deposition (e.g. chemical vapor deposition) techniques commonly used in the electronics industry.

The first substrate or sheet 30 may include a number of vias (not shown) to provide electrical communication between electrically conductive paths carried by the first and second faces 30a, 30b and/or inner layers of the first substrate or sheet 30. The vias may be composed of electric conductor or electrically conductive material received in a throughhole that extends between the first and second faces 30a, 30b, and/or between the inner layers, and/or between the first and/or second faces 30a, 30b and the inner layers of the first substrate or sheet 30.

The traces of conductor or conductive material may advantageously have dimensions that render the antennas 22 radiolucent or substantially radio-lucent. For example, the antennas 22 each may comprise a respective stripe-line aluminum coil having a number of windings, having a thickness that is not greater than 200 microns. For instance, each stripe-line aluminum coil may have a thickness that is not greater than 200 microns, and preferably not greater than 100 microns.

The mat based antenna and heater system 18 includes plurality of antennas 22, which may be positioned successively along at least a portion of a length of the first substrate or sheet 30. As illustrated, the antennas 22 may include a first set or linear (i.e., one-dimensional) array of antennas, for instance three coil antennas 22a-22c spaced along a length 31 of the first sheet 30, and a second set or linear array of antennas, for instance three coil antennas 22d-22f spaced along the length 31 of the first substrate or sheet 30, the second set or linear array of antennas spaced laterally across a width 33 of the first sheet 30 from the first set or linear of antennas 22a-22c. As illustrated, the first and second sets of antennas 22a-22c, 22d-22f may form a two-dimensional array. The two dimensional array of antennas 22 when driven a defined frequencies and power level may provide a biologically safe interrogation field that provides complete coverage over the body of a patient or portion thereof.

The one-, and advantageously, two-dimensional arrays of antennas 22 may, for example, be advantageously operated as a phased antenna array. Such operation may allow interrogation signals to be generally focused toward a location in a two dimensional plane parallel with a plane of the first substrate or sheet 30 and/or or focused at a desired or defined depth, the depth being measured generally orthogonally to the two-dimensional plan. Such operation may additionally, or alternatively, allow focused reception of response signals, for example generally focused toward a location in the two dimensional plane and/or or focused at a desired or defined depth. Such is not essential, since in many applications the two-dimensional array will provide adequate coverage and resolution to determine presence/absence without the use of phased array techniques.

Alternatively, the plurality of antennas 22 may include a greater or fewer number of antenna coils. For example, fewer antennas 22 may be employed for use in childbirth or delivery, as compared to environments employing standard operating room tables. The plurality of antennas 22 may include a different number of antennas 22 in the first set or linear array 22a-22c, than in the second set or linear array 22d-22f. The plurality of antennas 22 may include additional sets or linear arrays of antennas 22. Other arrangements of antennas 22 are possible. For example, the antennas 22 may not be arranged in sets, or may not be aligned in linear or two-dimensional arrays. Also for example, some antennas 22 may be staggered with respect to other ones of the antennas 22. Also for example, some antennas 22 may overlie other ones of the antennas 22, for example being carried on separate faces or layers of the first substrate or sheet 30. For instance, a third set of two antennas (not shown) may be carried on the second face 30b of the first substrate or sheet 30. Each of the antennas 22 of the third set may overlie a respective pair of antennas from each of the first set and the second sets of antennas. Thus, the antennas 22 of the third set may take the form of coils, each of which has a center which lies intermediate of the center points of a pair of antennas 22a, 22b or 22b, 22c from the first set, and which lies intermediate of the center points of a pair of antennas 22d, 22e or 22e, 22f from the second set. Likewise, the center of the antennas 22 of the third set may be positioned intermediate of the center points of a pair of antennas 22a, 22e or 22b, 22c or 22e, 22f from the first and second sets of antennas 22. Thus, the antennas 22 of the third set may be staggered in both dimensions of the plane of the first substrate or sheet 30 relative to the antennas 22 of the first and second sets. At least some of these arrangements of antennas 22 may be operated as a phased antenna array.

The antennas 22 may take forms other than coils, for example dipole or slot antennas, to name only a few. Additionally or alternatively, one or more passive or parasitic antenna elements may be carried one or more external or exterior faces or internal layers of the first substrate or sheet 30. Such may electromagnetically interact or cooperate with the active or driven antenna elements 22 generally described above. Such may, for example, focus the interrogation signals transmitted by the mat based antenna and heater system 18 and/or increase a reception range of the mat based antenna and heater system 18.

The mat based antenna and heater system 18 may include a first layer of silicon 32 carried by the upper face 30a of the first sheet. The mat based antenna and heater system 18 may additionally or alternatively include a second layer of silicon 34 carried by the lower second face 30b of the first substrate or sheet 30. Thus, the first substrate or sheet 30 and antennas 22 may be sandwiched between the first and second layers of silicon 32, 34. The first and/or the second layers of silicon 32, 34 are relatively stiff, and advantageously provide radius protection to the antennas 22 against bending about a radius of curvature that is so small or tight as to harm the conductive traces, for example via de-lamination, cleaving, splitting or cracking. The first and/or the second layers of silicon 32, 34 and the polyethylene film 30 may form a unitary, laminate structure. The silicon layers 32, 34 may advantageously be substantially radiolucent, to permit various imaging techniques to be employed. The silicon layers 32, 34 may, for example, be 0.125 inches thick, with a tolerance of plus or minus 0.0625 inches.

Notably, in use the mat based antenna and heater system 18 is subjected to numerous applications of bending, flexing, pulling and/or other sources of stress and/or strain. Such may, for example, occur when a patient is first placed onto the mat based antenna and heater system 18, when a patient is reoriented, or removed from mat based antenna and heater system 18, or simply when the patient moves. Such may also occur in normal handling of the mat based antenna and heater system 18 before, during or following use in a medical procedure. The repeated applications of stress and/or strain to the antennas 22, as well as to other fine components, lead to breaks or discontinuities which may greatly shorten the useful life of the mat based antenna and heater system 18. Inclusion of the silicon layers 32, 34 may surprisingly increase the number of uses of the mat based antenna and heater system 18 before structural failure, from less than approximately 50 uses to almost 1000 uses. Such may also facilitate the metal on metal welding (e.g., copper to aluminum), discussed below.

The mat based antenna and heater system 18 may include a gel layer 36 positioned relatively above the first layer of silicon 32 with respect to the first sheet 30. The gel layer 36 may, for example, take the form of a thermoplastic elastomer. The gel layer 36 may advantageously provide some protection to the underlying structure (e.g., antennas 22). The gel layer 36 may also provide some pressure relief to alleviate pressure points and reduce the development of ulcers or sores (e.g., commonly referred to as bed sores), on the patient, particular during long medical procedures. The gel layer 36 may additionally, or alternatively, advantageously provide thermal insulation for the patient. The gel layer 36 may advantageously be substantially radiolucent, to permit various imaging techniques to be employed. The gel layer 36 may, for example, be 0.25 inches thick, with a tolerance of plus or minus 0.125 inches.

The mat based antenna and heater system 18 may include a foam layer 38 spaced relatively above the gel layer 36 with respect to the first sheet 30. The foam layer 38 may, for example, comprise is a polyurethane foam. In particular, a closed cell polyurethane foam may be employed for resistance to water degradation and hence improved resistance to bacterial growth. The foam layer 38 may advantageously provide some protection to the underlying structure (e.g., antennas 22). The foam layer 38 may also provide some pressure relief to alleviate the development of ulcers or sores (e.g., commonly referred to as bed sores), on the patient and/or to provide thermal insulation for the patient. The foam layer 38 may advantageously be substantially radiolucent, to permit various imaging techniques to be employed. The foam layer 38 may, for example, be 0.375 inches thick, with a tolerance of plus or minus 0.125 inches.

The mat based antenna and heater system 18 may include a top cover sheet 40 spaced relatively above the foam layer 38 with respect to the first sheet 30. The top cover sheet 40 may, for example, take the form of a nylon polyurethane laminate. The nylon may advantageously be stretchable, allowing a tight, smooth fit, without creases or bulges. Such may advantageously reduce spots of inconsistent pressure which might otherwise give rise to bed sores. The polyurethane may enhance the ability to sterilize the mat based antenna and heater system 18 via conventional sterilization techniques. The top cover sheet 40 may, for example, be 0.025 inches thick, with a tolerance of plus or minus 0.005 inches.

The mat based antenna and heater system 18 may include a bottom cover sheet 42 spaced relatively below the second layer of silicon 34 with respect to the first sheet 30. The bottom cover 42 may advantageously take the form of a non-slip fabric, for instance a non-slip nylon, to retain the mat based antenna and heater system 18 in place on the patient support surface 12. The bottom cover sheet 42 may, for example, be 0.025 inches thick, with a tolerance of plus or minus 0.005 inches.

The heaters or heating elements 17 may be located above the foam layer 38 and beneath the cover sheet 40. Such places the heaters or heating elements 17 relatively close to the patient while still providing an electrically insulative layer therebetween. Alternatively, the heaters or heating elements 17 may be located relative below the foam layer 38, with the foam layer 38 in between the heaters or heating elements 17 and the patient. This may provide protection to the patient from any possible shock or burns should the current become excessive, although will typically require higher levels of current to achieve a desired warming effect than the illustrated embodiment.

The top and bottom cover sheets 40, 42, respectively, may be attached to one another to enclose the other components therein. For example, the top and bottom cover sheets 40, 42, respectively, may be attached about a periphery thereof. For instance, the top and bottom cover sheets 40, 42, respectively, may be attached via a radio frequency (RF) weld or seam to produce a hermetic and/or hemostatic seal. Alternatively, or additionally, the top and bottom cover sheets 40, 42, respectively, may be attached via one or more adhesives and/or stitches.

The mat based antenna and heater system 18 may optionally include a thermoplastic polyurethane sheet or layer 44 positioned between the first layer of silicon 32 and the gel layer 36. The polyurethane sheet or layer 44 may enhance the ability to sterilize the mat based antenna and heater system 18 via conventional sterilization techniques. The polyurethane sheet or layer 44 may, for example, be 0.0015 inches thick, with a tolerance of plus or minus 0.0005 inches.

The cable(s) 23, 25, 35 and cable interface head 29 provide a communications interface to communicatively coupling of the antennas 22 (FIGS. 1-3 and 5) with the console 16 (FIG. 1).

As best illustrated in FIG. 6, the cable head interface 29 includes a housing bottom 50a and a housing top 50b, the housing top 52b physically coupled to the housing bottom 50a to form a housing (collectively 50) having a cavity 54 therebetween. The housing bottom and top 50a, 50b may be make of a hard plastic (e.g., acrylonitrile-butadiene-styrene copolymer based, commonly referred to as ABS), to form a protective shell and prevent significant bending or flexing. The cable(s) 23, 25, 35 extend from the housing 50, to communicatively couple with the console 16 (FIG. 1).

The cable head interface 29 also includes a lower foam member 56 and an upper foam member 58 received in the cavity 54 between the housing bottom and housing top 50a 50b. The cable interface head 29 further includes a plurality of wires, collectively 60 (e.g., 22 AGW copper Litz wire), each of the wires 60 including an electrically insulative sheath 62 extending along at least a portion a length of the wire 60. The electrically insulative sheath 62 advantageously provide radius protection, preventing bending at such a small or tight radius of curvature that the wires 60 or electrical bonds (e.g., welds, solder) break or cleave. The wires 60 are protectively sandwiched between the lower and the upper foam members 56, 58, respectively. The foam may take variety of forms, for example polyurethane foam.

One end 60a of the wires 60 is electrically coupled to conductive traces on the first sheet or substrate 30 which form or lead to the antennas 22, or which form a resistive heater or heating element 17, and/or which couple to a sensor 19. Portions of the first and second silicon layers 32, 34 are visible in FIG. 6. In particular, portions of the wires 60 extending from the sheaths or tubing 62 may be tinned and ultrasonically welded to the conductive traces that form the antennas 33, or which form a resistive heater or heating element 17, and/or which couple to a sensor 19. For instance, copper Litz wires may be metal-to-metal ultrasonically welded to aluminum traces that form the antennas 22. The other end 60b of the wires 60 may be soldered to respective terminal contacts 64 on a cable head interface printed circuit board 66, which is also received in the cavity 54 between the housing bottom and housing top 50a, 50b.

A hard epoxy 68 (e.g., two-part epoxy resin and catalyst) is applied to each connection (e.g., ultrasonic weld) of the wire 60 to the respective conductive traces which form the antennas 22. The hard epoxy 68 may advantageously extend over portions of the sheaths 62. The hard epoxy 68 helps protect the connections (e.g., ultrasonic welds) between the wires 60 to the traces, and provides rigid protection to the connections. Again, the resulting structure may provide radius protection against over bending, as well as providing some protection against tensile loads such as those that would be exerted by pulling on the cable(s) 23, 25, 35. A soft epoxy 70 may fill the area surrounding the connection (e.g., ultrasonic weld) of the wire 60 to the respective conductive traces (e.g., aluminum) which form the antennas 22. The soft epoxy 70 advantageously provides a more resilient protection than the hard epoxy 68. Additionally, a piece of foam 59 may be interposed between the soft epoxy and the silicon layer 32 on the first substrate or layer 30. The foam may, for example take the form of a piece of weather stripping or similar foam product. Such can provide additional protection to the circuit structure.

The cable interface head 29 may also includes a lower layer of a double sided electrically insulative tape 72 (e.g., polyester tape) positioned between the lower foam member 56 and the bottom cover sheet 42. The double sided electrically insulative tape 64 may adhesively retain the bottom cover sheet 42 to the lower foam member 56. The cable interface head 29 may further include an upper layer of a double sided electrically insulative tape 74 (e.g., polyester tape) positioned between the upper foam member 58 and the top cover sheet 40. The double sided electrically insulative tape 66 may adhesively retain the top cover sheet 40 to the upper foam member 58. The double sided electrically insulative tape 72, 74 may extend inward along the tab 27, and be adhered to the first and the second silicon layers 32, 34. For example, the double sided electrically insulative tape 72, 74 may be adhered to the silicon 32, 34 on both sides of a tail of the conductive traces, and extend into the assembly of antenna coils 22, some distance or length, for instance 200 millimeters. Such provides a secure physical coupling between the cable interface head 29 and the first substrate or sheet 30, helping to ensure robust electrical connectivity between the wires 60 and the electrical traces which from the antennas 22.

The cable interface head 29 may also advantageously include a electrically insulative tape 76 positioned between the foam and the conductive traces that form the antennas 22, or which form a resistive heater or heating element 17, and/or which couple to a sensor 19. The electrically insulative tape 76 should employ a relatively low tack adhesive. Such may advantageously prevent stress and strains being applied via the electrically insulative tape 76 from breaking the conductive traces. A polyester blend tape may not suitable, but rather a polyimide tape may be advantageously employed, such as those polyimide tapes sold under the trademark KAPTON®.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

For example, while illustrated as a single mat based antenna and heater system 18, each patient support structure 12 may carry one or more mat based antenna and heater system 18. The mat based antenna and heater system 18 may take a variety of forms, and may be disposable, or may be capable of withstanding multiple cycles of sterilization (e.g., chemical, heat, radiation, etc.). As previously explained, the mat based antenna and heater system 18 is preferably radiolucent.

While illustrated as including a gel layer 36 and a foam layer 38, the mat based antenna and heater system 18 may alternatively, or additionally include one or more bladders (e.g., dual layer urethane envelope) to receive a fluid (e.g., air, water, etc.) to selectively inflate one or more portions of the mat based antenna and heater system 18, and/or to control a temperature of one or more portions of the mat based antenna and heater system 18. In such embodiments, the fluid should be radiolucent. In such embodiments, the cushioning gel or polymer material should be radiolucent. The cushioning layer may include recesses or voids formed at locations selected to accommodate a patient's anatomy.

As described above, portions of one or more of the antennas 22 may overlap. For example, where the antennas 22 are coil antennas, each formed of one or more coils, a portion of an area enclosed by an outermost coil of each antenna 22 may overlap a portion of an area enclosed by an outermost coil of a neighboring antenna 22. The area enclosed or enclosed area may be an area enclosed by a normal or perpendicular projection of a perimeter defined the outermost coil of the respective antenna 22. In such embodiments, neighboring antennas 22 may be electrically insulated from one another by one or more electrically insulating layers or substrates. For example, successively adjacent antennas 22 may be carried one opposite surfaces (e.g., opposed outer surfaces, or multiple inner surfaces, or one or more outer and inner surfaces) of a single substrate 30.

As discussed above, the antennas 22 may advantageously be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent, and more preferably, a thickness of 100 microns or less. An antenna may be considered radiolucent if it is not detectable by a radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by a radiologist in an X-ray.

While generally discussed in terms of electric heaters or heating elements 17 which are an integral portion of the mat, the mat based antenna and heater system 18 may employ other forms or configurations of heaters. For example, a heater may be a separate and distinct element or structure from the mat. The separate and distinct heater may be fluidly coupled to one or more capillaries or fluid passages formed in the mat. The separate and distinct heater may heat fluids (e.g., liquid, gas, vapor) and pass the heated fluids through the capillaries or fluid passages of the mat. The separate and distinct heater may include or may be coupled to one or more pumps, fans or blowers to cause the heated fluid to pass through the capillaries or fluid passages of the mat. Fluids may include fluids that have a relatively high heat capacity, e.g., a heat transfer fluid that is a eutectic mixture of two very stable compounds, biphenyl ($C_{12}H_{10}$) and diphenyl oxide ($C_{12}H_{10}O$) commercially available from Dow Chemical Company under the mark DOWTHERM™.

Also for example, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. To the extent not inconsistent with the teachings herein, all U.S. patents, U.S. patent application publications, U.S. patent applications, foreign patents, foreign patent applications and non-patent publications commonly owned with this patent application and referred to in this specification and/or listed in the Application Data Sheet including: U.S. Patent Publication No. US 2004/0250819, published Dec. 16, 2004; U.S. Provisional Patent Application No. 60/811,376 filed Jun. 6, 2006; U.S. Provisional Patent Application No. 61/109,104 filed Oct. 28, 2008; U.S. Provisional Patent Application No. 61/222,443 filed Jul. 1, 2009; U.S. Provisional Patent Application No. 61/222,847 filed Jul. 2, 2009; U.S. Provisional Patent Application No. 61/242,699, filed Sep. 15, 2009; U.S. provisional patent application Ser. No. 61/242,704 filed Sep. 15, 2009; U.S. Non-Provisional patent application Ser. No. 11/743,104 filed May 1, 2007; U.S. Non-Provisional patent application Ser. No. 12/472,199 filed May 26, 2009; U.S. Non-Provisional patent application Ser. No. 12/473,059 filed May 27, 2009; U.S. patent application Ser. No. 12/606,688 filed Oct. 27, 2009, published as U.S. patent application publication 2010-0109848, U.S. Pat. No. 6,026,818, issued Feb. 22, 2000; and U.S. patent application Ser. No. 13/422,192, filed Mar. 16, 2012, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A mat based antenna and heater system for use in detecting transponder tagged objects which are used in performing medical procedures, the mat based antenna and heater system comprising:
   a first sheet of an electrically insulative material that is sized to support at least a portion of a patient, the first sheet having an upper face and a lower face opposed to the upper face;
   a plurality of antennas positioned successively along at least a portion of a length of the first sheet, the antennas sized and dimension to oscillate in at least one of an RF or microwave frequency range in response to a signal;
   a first layer of silicon carried by the upper face of the first sheet;
   a second layer of silicon carried by the lower second face of the first sheet;
   a gel layer positioned relatively above the first layer of silicon with respect to the first sheet;
   a foam layer spaced relatively above the gel layer with respect to the first sheet; and
   at least one electrical resistance heater element positioned along at least a portion of length of the foam layer, the at least one electrical resistance heater element sized and dimension to dissipate heat in response to a current passing therethrough without oscillation in at least one of the RF or microwave frequency range.

2. The mat based antenna and heater system of claim 1, further comprising:
   a top cover sheet spaced relatively above the foam layer with respect to the first sheet.

3. The mat based antenna and heater system of claim 2 wherein the top cover is a nylon polyurethane laminate.

4. The mat based antenna and heater system of claim 2, further comprising:
   a bottom cover sheet spaced relatively below the second layer of silicon with respect to the first sheet.

5. The mat based antenna and heater system of claim 4 wherein the bottom cover is a non-slip fabric.

6. The mat based antenna and heater system of claim 4, further comprising:
   a thermoplastic polyurethane positioned between the first layer of silicon and the gel layer.

7. The mat based antenna and heater system of claim 6 wherein the first sheet is a polyethylene film.

8. The mat based antenna and heater system of claim 7 wherein the antennas are traces of metal carried by the polyethylene film and the traces have dimensions that make the antennas radiolucent.

9. The mat based antenna and heater system of claim 8 wherein the polyethylene film and the first and the second silicon layers form a unitary laminate structure.

10. The mat based antenna and heater system of claim 7 wherein the antennas each comprise a respective stripe-line aluminum coil having a number of windings, each stripe-line aluminum coil having a thickness that is not greater than 200 microns.

11. The mat based antenna and heater system of claim 10 wherein each stripe-line aluminum coil has a thickness that is not greater than 100 microns.

12. The mat based antenna and heater system of claim 6 wherein the foam layer is a polyurethane foam.

13. The mat based antenna and heater system of claim 6 wherein the gel layer is a thermoplastic elastomer.

14. The mat based antenna and heater system of claim 2 wherein the at least one electrical resistance heater element is carried between the foam layer and the bottom cover sheet.

15. The mat based antenna and heater system of claim 1 wherein the at least one electrical resistance heater element is carried on a top surface of the foam layer under the top cover sheet.

16. The mat based antenna and heater system of claim 1 wherein the antennas include a first set of three coil antennas spaced along the length of the first sheet, and a second set of three coil antennas spaced along the length of the first sheet, the second set of antennas spaced laterally across a width of the first sheet from the first set of antennas.

17. The mat based antenna and heater system of claim 1, further comprising:
   at least one cable interface head to allow selective communicative coupling of a controller with the antennas and the at least one electrical resistance heater element.

18. The mat based antenna and heater system of claim 17 wherein the at least one cable interface head includes an upper foam member, a lower foam member, and a plurality of wires, each of the wires including an electrically insulative sheath along at least a portion thereof, the wires protectively sandwiched between the upper and the lower foam members.

19. The mat based antenna and heater system of claim 18 wherein the at least one cable interface head further includes a housing bottom and a housing cover, the housing cover physically coupled to the housing bottom, the upper and the lower foam members sandwiched between the physically coupled housing bottom and cover.

20. The mat based antenna and heater system of claim 19 wherein the at least one cable interface head further includes an upper layer of an electrically insulative tape positioned between the upper foam member and a lower layer of an electrically insulative tape positioned between the lower foam member and the housing bottom.

21. The mat based antenna and heater system of claim 20 wherein the at least one cable interface head further includes a soft epoxy member and a hard epoxy member positioned opposed to one another proximate a location where the wires are electrically coupled to a number of conductive traces carried by the first sheet of electrically conductive material.

22. The mat based antenna and heater system of claim 21, further comprising:

a cable carrying the plurality of wires; and an interface head having a housing bottom, a housing cover, and a plurality of communicative paths extending therethrough, the communicative paths communicatively coupling the antennas of the mat based antenna and heater system and the wires of the cable.

23. A mat based antenna and heater system for use in detecting transponder tagged objects which are used in performing medical procedures, the mat based antenna and heater system comprising:

a first sheet of an electrically insulative material that is sized to support at least a portion of a patient, the first sheet having an upper face and a lower face opposed to the upper face;

a plurality of antennas positioned successively along at least a portion of a length of the first sheet, the antennas formed of a first electrically conductive material having a first resistivity;

a first layer of silicon carried by the upper face of the first sheet;

a second layer of silicon carried by the lower second face of the first sheet;

a gel layer positioned relatively above the first layer of silicon with respect to the first sheet;

a foam layer spaced relatively above the gel layer with respect to the first sheet; and at least one electrical resistance heater element positioned along at least a portion of length of the foam layer, the at least one electrical resistance heater element formed of a second electrically conductive electrically conductive material having a second resistivity, the second resistivity substantially higher than the first resistivity.

24. The mat based antenna and heater system of claim 23 wherein the second resistivity at least approximately 49 micro-ohms·cm at 20° C.

25. The mat based antenna and heater system of claim 23 wherein the at least one electrical resistance heater element dissipates approximately 0.2-0.5 watts/square inch.

26. The mat based antenna and heater system of claim 23 wherein the at least one electrical resistance heater element comprises at least one of a carbon fiber, a nickel-chromium alloy, a cupronickel alloy, a Kanthal alloy (FeCrAl), an etched foil, a ceramic heating element, a silicone rubber insulated heater wire, a polyimide film insulated heater, or a stainless steel resistor element.

* * * * *